US007700581B2

(12) United States Patent
Chen et al.

(10) Patent No.: US 7,700,581 B2
(45) Date of Patent: Apr. 20, 2010

(54) CEPHALOSPORIN COMPOUNDS COMPRISING A C3 THIO-METHYL MOIETY SUBSTITUTED WITH N-CONTAINING HETEROCYCLIC GROUP, AND A C7 THIOUREA ACETAMIDO GROUP, THEIR PREPARATIONS AND USES THEREOF

(75) Inventors: Mao Chen, Guangdong (CN);
Shaoxuan Zhu, Guangdong (CN);
Xuebin Liu, Guangdong (CN); Chun Luo, Guangdong (CN); Shuwen Xu, Guangdong (CN); Lizhen Zheng, Guangdong (CN); Fang Ye, Guangdong (CN); Chenglong Yi, Guangdong (CN); Xiaona Zhang, Guangdong (CN)

(73) Assignee: Guangzhou Baiyunshan Pharmaceutical Co., Ltd., Guangzhou, Guangdong (CN)

( * ) Notice: Subject to any disclaimer, the term of this patent is extended or adjusted under 35 U.S.C. 154(b) by 557 days.

(21) Appl. No.: 11/700,087

(22) Filed: Jan. 31, 2007

(65) Prior Publication Data
US 2008/0182836 A1 Jul. 31, 2008

(51) Int. Cl.
*C07D 501/36* (2006.01)
*A61K 31/545* (2006.01)
*A61K 31/546* (2006.01)
*A61P 31/04* (2006.01)

(52) U.S. Cl. .................. 514/204; 514/206; 514/208; 540/226; 540/227; 540/229

(58) Field of Classification Search ............... 540/226, 540/227; 514/204, 206, 208
See application file for complete search history.

(56) References Cited

U.S. PATENT DOCUMENTS 3,516,997 A * 6/1970 Masaru et al. .............. 540/227
3,929,779 A * 12/1975 Bickel et al. ............... 540/227
3,989,687 A * 11/1976 Bambury et al. ........... 540/328
4,017,488 A * 4/1977 Hiraoka et al. ............. 540/221
4,254,260 A * 3/1981 Takaya et al. .............. 540/227

FOREIGN PATENT DOCUMENTS

CN 1727347 A * 2/2006

* cited by examiner

*Primary Examiner*—Mark L Berch
(74) *Attorney, Agent, or Firm*—Finnegan, Henderson, Farabow, Garrett & Dunner, L.L.P.

(57) ABSTRACT

Disclosed herein are a cephalosporin compound of formula I,

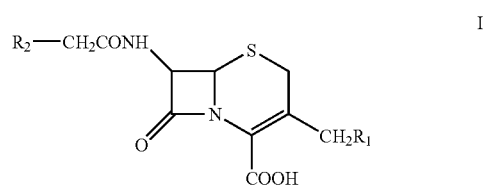

wherein $R_1$ is selected from the following groups:

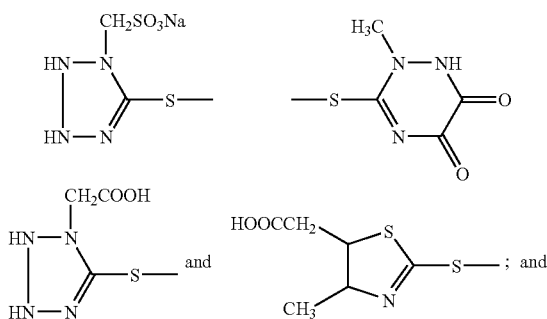

wherein $R_2$ is selected from the following groups:

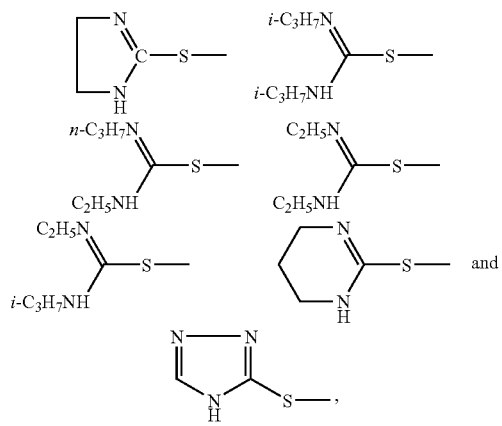

the preparation and uses thereof. A method of preparing the cephalosporin compound as disclosed herein comprises reacting a starting cephalosporin comprising a C7 amino group and a C3 thio-methyl moiety substituted with an N-containing heterocyclic group with bromoacetyl bromide and then with a N,N'-bissubstituted thiourea. Methods of treating an infectious disease are also disclosed, comprising administering to a patient in need thereof the pharmaceutical composition disclosed herein.

19 Claims, 2 Drawing Sheets

CEPHALOSPORIN COMPOUNDS COMPRISING A C3 THIO-METHYL MOIETY SUBSTITUTED WITH N-CONTAINING HETEROCYCLIC GROUP, AND A C7 THIOUREA ACETAMIDO GROUP, THEIR PREPARATIONS AND USES THEREOF

The present invention generally relates to novel cephalosporin compounds comprising a C3 thio-methyl moiety substituted with an N-containing heterocyclic group, and a C7 thiourea acetamido group. The present invention also relates to compositions comprising the novel cephalosporin compounds. In addition, the present invention relates to preparations and uses of the novel cephalosporin compounds.

Cephalosporins in general possess excellent antibacterial activity and have low toxicity to mammals. They are thus useful medicines to cure the infectious diseases of mammals.

As cephalosporin-type antibiotics are widely used in clinics, resistance to these medicines has occurred. For example, the infectious diseases caused by methicillin-resistant *staphylococcus aureus* (MRSA), penicillin-resistant pneumococci (PRSP), and antibiotic-resistant *enterococcus* have become serious clinical problems. Therefore, there is a strong demand for new cephem antibiotics in order to increase the antibacterial activity to those bacteria.

Known cephalosporins modified on the C7 position mainly include those having aminothiazole glyoxylamido side chains such as ceftriaxone and cefotaxime as shown below.

Known cephalosporins modified on the C7 position also include those containing phenylglycine groups such as cefalexin and cefradine. However, the modifications of pharmacokinetics mainly focus on introducing functional groups on the C3 position of cephalosporins. Currently, studies on structural modifications of cephalosporin C on the C3 position have become popular. It has been found that substituting an —OCOCH$_3$ (—OAc) group on the C3 position of cephalosporin C with S- or N-containing groups can enhance and broaden its antibacterial effectiveness. For example, substituting 7-ACA on the C3 position with an S-containing heterocyclic substituent can significantly increase the antibacterial activity of the cephalosporin to Gram-positive and Gram-negative bacteria and increase the stability under β-lactamase. See CHINESE JOURNAL OF ANTIBIOTICS, 1988, Vol. 252. Examples of C3 substituted with a tetrazole mercapto group include cefoperazone and cefmetazole. Examples of C3 substituted with a triazin mercapto group include ceftriaxone. Examples of C3 substituted with a thiodiazole group include cefazolin and cefuzonam. Examples of introducing an acidic functional substitutent on the C3 position to extend the half-life and to obtain prolonged and high medical effectiveness include ceftriaxone and cefonicid.

Introducing a functional group to the basic cephalosporin 7-ACA on its C3 position produces different intermediates such as (6R,7R)-7-amino-3-[[2,5-dihydro-6-hydroxy-2-methyl-5-oxo-1,2,4-triazin-3-yl]thio]-methyl]-8-oxo-5-thia-1-azabicyclo-[4.2.0]oct-2-ene-2-carboxylic acid ("7-ACT") and 7-amino-3-[[[5-(carboxymethyl)-4-methyl-2-thiazolyl]thio]methyl]-8-oxo-5-thia-1-aza-bicyclo[4.2.0]oct-2-ene-2-carboxylic acid ("7-TACS"), which are commercially available pharmaceutical intermediates. Condensation reaction of the free amino group of these intermediates with various thioureas can produce a series of cephalosporin derivatives that have anti Gram-positive and anti Gram-negative activities. These derivatives can also have increased stability under β-lactamase and an extended pharmacokinetic lifetime.

Cefathiamidine is a cephalosporin derivative obtained by substituting N,N'-diisopropylthiourea on the C7 position of 7-ACA. It has a relatively high anti Gram-positive bacteria activity, but undesirably low anti Gram-negative bacteria activity. Further, it has a short pharmacokinetic half-life, fast drug clearance, and relatively low bioavailability. To overcome at least one of these problems, the present inventors have found that introducing a triazine group to the C3 position of ceftriaxone in the structure of cefathiamidine could produce novel cephalosporin compounds, which can have the similarly high anti Gram-positive activity as cefathiamidine, but can overcome at least the short pharmacokinetic half life, and thus improve the bioavailability.

The present inventors have also found that the combination of the modifications on the C3 and the C7 positions can extend the antibacterial spectrum of cephalosporin, increase its anti Gram-positive bacteria activity, and enhance its bioavailability and commercial feasibility.

Therefore, disclosed herein are novel cephalosporin derivatives, such as those that can be used to cure Gram-positive bacteria infections.

Further disclosed herein are methods for the preparation of the novel cephalosporin derivatives.

Even further disclosed herein are pharmaceutical compositions comprising at least one of the novel cephalosporin derivatives. The pharmaceutical compositions may be in a form known to one of ordinary skill in the pharmaceutical art, including, for example, a pill, tablet, lozenge, coated tablet, granule, capsule, hard or soft gelatin capsule, aqueous solution, alcoholic solution, oily solution, syrup, emulsion suspension pastille suppository, solution for injection or infusion, ointment, tincture, cream, lotion, powder, spray, transdermal therapeutic systems, nasal spray, aerosol mixture, microcapsule, implant, rod or plaster.

Even further disclosed herein are methods of treating an infectious disease comprising administering to a patient in need thereof a pharmaceutical composition disclosed herein. In one embodiment, the infectious disease is an antibiotic-resistant disease, such as antibiotic-resistant *enterococcus*.

One embodiment of the present invention is directed to a cephalosporin compound comprising a C3 thio-methyl moiety substituted with an N-containing heterocyclic group, and a C7 thiourea acetamido group, or a pharmaceutically acceptable salt thereof, the cephalosporin compound having the following general formula I:

wherein: $R_1$ is selected from the following groups:

$R_2$ is selected from the following groups:

The cephalosporin compounds disclosed herein may be in free state or in a state such as a solvate. In one embodiment, the cephalosporin compound has the following formula II:

In this embodiment, the compound's chemical name is 3-((1,2,5,6-tetrahydro-2-methyl-5,6-dioxo-1,2,4-triazine-3-ylthio)methyl)-7-[[[[[(1-methylethyl)amino][(1-methylethyl)imino]methyl]thio]acetyl]amino]-8-oxo-5-thia-1-azabicyclo[4.2.0]oct-2-ene-2-carboxylic acid (referred hereinafter as "BYS02"). BYS02 can be in a form, for example, of its hydrobromide salt or amine salt.

The compounds of general formula I can also be chosen, for example, from the following compounds of formulae III-V:

The cephalosporin compounds of formula I can be prepared, for example, by a method comprising:

1. dissolving or suspending a starting cephalosporin compound with a C7 amino group and a C3 thio-methyl moiety substituted with an N-containing heterocyclic group in a suitable solvent, and adjusting the pH value of the mixture with an organic or inorganic base to obtain a solution;

2. reacting the resulting solution with 2-bromoacetyl bromide;

3. acidifying the resulting mixture of step 2;

4. reacting the resulting product of step 3 with an N,N'-bissubstituted thiourea; and

5. isolating the product from the reaction mixture of step 4.

The suitable solvent in step 1 can be chosen from those commonly used in the art. For example, the suitable solvent in step 1 can be chosen from ketones, alcohols, such as aliphatic alcohols, halides, such as alkyl halides, and mixtures thereof. The ketones can be chosen, for example, from acetone and methyl isobutyl ketone. The aliphatic alcohols can be chosen, for example, from methanol, ethanol, and isopropanol. The alkyl halide can be, for example, methylene dichloride.

In step 1, the organic base can be chosen from those commonly used in the art. For example, the organic base can be chosen from triethylamine, diethylamine, tributylamine, and tetramethyl guanidine. The inorganic base can also be chosen from those commonly used in the art. For example, the inorganic base can be chosen from sodium bicarbonate, sodium carbonate, and ammonium.

In step 3, the acidification can use at least one acid chosen from those commonly used in the art. For example, the at least one acid can be chosen from hydrochloric acid, sulfuric acid, acetic acid, and phosphoric acid. In one embodiment, the resulting mixture of step 2 is acidified to a pH value of less than 7, such as, for example, less than 5, and less than 3.

In the method disclosed herein, the starting cephalosporin compound can be of, for example, formula VI:

wherein $R_1$ is defined the same as in general formula I. The N,N'-bissubstituted thiourea used in step 4 can be selected from the following compounds:

For example, in one embodiment of the present invention, BYS02 is prepared by reacting (6R,7R)-7-amino-3-[[2,5-di-hydro-6-hydroxy-2-methyl-5-oxo-1,2,4-triazin-3-yl]thio]-methyl]-8-oxo-5-thia-1-azabicyclo-[4.2.0]oct-2-ene-2-carboxylic acid with 2-bromoacetyl bromide to produce 3-((1,2,5,6-tetrahydro-2-methyl-5,6-dioxo-1,2,4-triazin-3-ylthio)methyl)-7-(2-bromoacetamido)-8-oxo-5-thia-1-aza-bicyclo[4.2.0]oct-2-ene-2-carboxylic acid and then reacting the product with 1,3-diisopropylthiourea to produce BYS02. The reactions are shown as follows.

In one embodiment, the method of preparing BYS02 disclosed herein comprises the following steps.

1. Dissolving or suspending (6R,7R)-7-amino-3-[[2,5-di-hydro-6-hydroxy-2-methyl-5-oxo-1,2,4-triazin-3-yl]thio]methyl]-8-oxo-5-thia-1-azabicyclo-[4.2.0]oct-2-ene-2-carboxylic acid ("7-ACT") in a suitable solvent. The suitable solvents can contain water or be anhydrous, chosen, for example, from ketones, for example, $C_1$-$C_6$ alkyl ketones such as acetone, methyl isobutyl ketone, and ethyl ketone; $C_1$-$C_6$ alcohols such as methanol, ethanol, and isopropanol; nitrites such as propionitrile; amides such as dimethyl acetamide, and dimethyl formamide; and mixtures thereof.

2. Adjusting the pH value of the mixture using an organic base, such as an organic amine, or an inorganic base to make a clear solution. The organic amine can be chosen, for example, from triethylamine, diethylamine, and tributylamine. The inorganic base can be chosen, for example, from sodium carbonate, sodium bicarbonate, and ammonium.

3. Reacting the clear solution of step 2 with bromoacetyl bromide. Each mole of 7-ACT requires, for example, from 0.5 to 3.0 ml, such as from 1.2 to 2.4 ml, of bromoacetyl bromide. The reaction temperature ranges, for example, from 0 to 50° C., such as from 10 to 40° C. The reaction time ranges, for example, from 10 to 60 minutes or until the reaction mixture becomes a clear solution.

4. Acidifying the resulting mixture of step 3 using an acid chosen, for example, from hydrochloric acid, sulfuric acid, acetic acid, and phosphoric acid and isolating the product.

5. Dissolving or suspending the resulting product of step 4 in a solvent to react with N,N'-diisopropylthiourea. The molar ratio of bromoacetyl 7-ACT to N,N'-diisopropylthiourea ranges, for example, from 1.0 to 4.0, such as from 1 to 2.5, and further such as from 1.2 to 1.8. The reaction temperature ranges, for example, from 0 to 42° C. The reaction time ranges, for example, from 30 to 300 minutes. The solvent in step 5 can be chosen, for example, from alkyl halides, ketones, alcohols, and mixtures thereof.

6. Isolating the resulting product from the reaction mixture of step 5. The separation (i.e., isolation) may use common methods known in the art, for example, adding a solvent to precipitate the product while keeping the byproducts and impurities in the mother liquid. The product purity can reach, for example, 90% or higher.

The solvent in step 6 can be chosen, for example, from ketones, alcohols, nitriles, and mixtures thereof. Examples of the ketones include acetone and methyl isobutyl ketone. Examples of the alcohols include methanol and ethanol. Examples of the nitrile include propionitrile.

Further disclosed herein is an intermediate cephalosporin product of formula VII:

VII wherein $R_1$ is defined the same as above.

Further disclosed herein is a method of preparing the above cephalosporin intermediate of formula VII, comprising reacting the compound of general formula VI with bromoacetyl bromide following steps 1-4 of the method as set forth above.

Further disclosed herein is a pharmaceutical composition comprising (a) at least one compound chosen from the compounds of formulae I and II and pharmaceutically acceptable salts thereof, and (b) a pharmaceutically acceptable carrier.

For example, the pharmaceutical composition disclosed herein can be used as an antibiotic.

In vitro antibacterial activity test of the cephalosporin compounds disclosed herein using the common methods known in the art were conducted. The following table shows the minimum inhibitory concentration (MIC) (mg/l) of the cephalosporin compounds disclosed herein over various bacteria and the comparison with ceftriaxone.

From the above table, it can be seen that the cephalosporin compounds disclosed herein have a high antibacterial activity to *staphylococcus aureus, staphylococcus epidermidis, streptococcus pyogenes, streptococcus pneumoniae*, and *streptococcus hemolyticus* group A and *streptococcus hemolyticus* Group B; an antibacterial activity to *enterococcus*; a moderate antibacterial activity or resistance to *salmonella, shigella*, and *hemophilus influenzae*; and no antibacterial activity to *pseudomonas aeruginosa*. These results indicate that the cephalosporin compounds disclosed herein can have strong or relatively strong antibacterial activity to Gram-positive bacteria, and have antibacterial activity to some of Gram-negative bacteria.

The cephalosporin compounds disclosed herein can be modified from the third generation cephalosporins such as ceftriaxone, cefodizime, cefonicid, and ceforanide, maintaining their C3 functional substituent but introducing on the C7 position a N,N'-diisopropylthiourea group. The third generation cephalosporins have good sensitivity to Gram-negative bacterial such as *E. coli, hemophilus influenzae*, etc., but relatively poor sensitivity to antibiotic-resistant *pseudomonas aeruginosa* and most Gram-positive bacterial including *enterococcus*.

Through introducing an N,N'-diisopropylthiourea group to the C7 position of the cephalosporin nuclear, the cephalosporin compounds disclosed herein can be obtained. Compared to the third generation of cephalosporins, the cephalosporin compounds disclosed herein can have significantly increased antibacterial activity to Gram-positive bacteria, such as to *staphylococcus aureus* and *enterococcus*, and thus can extend the antibacterial spectrum. Also, compared to the first generation of cephalosporin such as cefathiamidine, the introduction of the C3 acidic functional group can prolong the half-life of the cephalosporin compounds disclosed herein, thus achieving long-effectiveness and bioavailability, as shown in the following examples.

|  | Compound II | Compound III | Compound IV | Compound V | Ceftriaxone |
|---|---|---|---|---|---|
| *Staphylococcus aureus* | 1-4 | 0.25-0.5 |  | 0.25-2 | 32-64 |
| *Staphylococcus epidermidis* | 0.0312-2 |  | 0.5-2 |  | 2-8 |
| *Streptococcus hemolyticus* group A |  |  | 2-8 | 0.125-1 |  |
| *Streptococcus hemolyticus* Group B |  | 0.25-4 | 0.5-1 |  |  |
| *Viridans streptococcus* |  |  |  | 0.125-4 |  |
| *Enterococcus* | 4-8 | 4-8 |  | 2-8 | >512 |
| *Streptococcus pyogenes* |  | 0.125-1 |  | 0.0312-0.5 |  |
| *Streptococcus pneumoniae* | 0.125-0.5 |  | 0.25-0.5 |  |  |
| *Salmonella* |  |  | 8-16 | 2-8 | 0.125 |
| *Shigella* |  | >64 | 16-256 |  |  |
| *Pseudomonas aeruginosa* | >512 | >256 | >512 |  |  |
| *Hemophilus influenzae* | 8-16 | 8-64 |  | >256 |  |

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The examples that follow are intended to illustrate the disclosure without, however, limiting its scope.

EXAMPLES

The following examples illustrate the preparation of 3-((1, 2,5,6-tetrahydro-2-methyl-5,6-dioxo-1,2,4-triazine-3-yl) thio)methyl)-7-[[[[[(1-methyl ethyl)amino][(1-methylethyl) imino]methyl]thio]acetyl]amino]-8-oxo-5-thia-1-aza-bicyclo[4.2.0]oct-2-ene-2-carboxylic acid ("BYS02").

I. Preparation of Intermediate

Example 1

50 ml of toluene, 50 ml of water and 5 g of (6R,7R)-7-amino-3-[[2,5-dihydro-6-hydroxy-2-methyl-5-oxo-1,2,4-triazin-3-yl]thio]-methyl]-8-oxo-5-thia-1-azabicyclo-[4.2.0] oct-2-ene-2-carboxylic acid (7-ACT) were added to a three-neck flask. 3.4 ml of triethylamine was added dropwise to the flask with stirring to dissolve 7-ACT. 3 ml of bromoacetyl bromide and 30 ml of 5% $NaHCO_3$ aqueous solution were added to the reaction mixture. After 2 hours of reaction, the stirring was stopped and the reaction mixture was put aside for phase separation. The organic phase was removed. The aqueous phase was acidified to a pH value of 3 and underwent crystallization at a temperature of 0-10° C. for 2 hours. The solid was filtered and dried under vacuum to yield 4 g of the intermediate, i.e., 3-((1,2,5,6-tetrahydro-2-methyl-5,6-dioxo-1,2,4-triazin-3-yl)thio)methyl)-7-(2-bromoacetamido)-8-oxo-5-thia-1-aza-bicyclo[4.2.0]oct-2-ene-2-carboxylic acid.

Example 2

60 ml of ethyl acetate, 60 ml of water, and 5 g of 7-ACT were added to a three-neck flask. 3.4 ml of triethylamine was added to the reaction mixture at a temperature of 0-10° C. with stirring until the solid 7-ACT was completely dissolved. 4 ml of bromoacetyl bromide was added to the reaction mixture; and then additional 2 ml of triethylamine was added. After the reaction, the mixture was acidified to a pH value of 3 and stayed for 2 hours. The solid product is filtered and dried under vacuum to yield 3.3 g of the intermediate.

Example 3

60 ml of propionitrile, 60 ml of water, and 5 g of 7-ACT were added to a three-neck flask. 3.6 ml of triethylamine was added to the reaction mixture at a temperature of 0-10° C. with stirring until the solid 7-ACT was dissolved. 4 ml of bromoacetyl bromide and 30 ml of 15% $NaHCO_3$ aqueous solution were added to the reaction mixture. After the completion of the reaction, the mixture was acidified to a pH value of 3. The solid was formed and crystallized for 2 hours. The solid was filtered and dried under vacuum to yield 4.9 g of the intermediate.

Example 4

250 ml of methylene dichloride, 250 ml of water, and 5 g of 7-ACT were added to a three-neck flask. Triethylamine was added to the mixture dropwise until the solid 7-ACT was dissolved. 4 ml of bromoacetyl bromide was added to the flask and a large amount of solid product was formed. The reaction continued for 2 hours and the reaction mixture was set aside for phase separation. The organic phase was removed. The aqueous phase was acidified with hydrochloric acid to a pH value of 3. After 2 hours of crystallization, the solid was filtered, washed with water, and dried under vacuum to yield 3.2 g of the intermediate.

Example 5

50 ml of acetone, 50 ml of water, and 5 g of 7-ACT were added to a three-neck flask. Triethylamine was dropwise added to the flask until the solid 7-ACT was dissolved. 4 ml of bromoacetyl bromide and 100 ml of 5% $NaHCO_3$ aqueous solution were added to the flask. The reaction continued for one hour and the resulting mixture was acidified with hydrochloric acid to a pH value of 3. A large amount of solid product was formed. The crystallization continued for 2 hours, and the resulting solid was filtered, washed with water, and dried under vacuum to yield 4 g of the intermediate.

II. Preparation of BYS02

Example 6

200 ml of methylene dichloride and 2.0 g of the intermediate prepared according to Example 1 were added to a three-neck flask. 16 ml of triethylamine was added dropwise to the flask to dissolve the solid. 0.6 g of N,N'-diisopropylthiourea was added to the reaction mixture. The mixture was refluxed until the reaction was complete. A solid product appeared in the reaction mixture. The temperature was lowered and the crystallization was carried out for an hour. The solid was filtered and dried under vacuum to yield 1.5 g of the product. It has a pH value of 5.4 and cloudiness of lower than 1 degree (1 g/10 ml water). The product is water soluble.

The product was analyzed by $H^1$—NMR (DMSO-$d_6$, 500 Hz) with the following result: 1.13 (m, 12H, —CH—CH3), 3.03 (q, 2H, J=22.0, 7.0 Hz, —S—NH—CH—), 3.04, 3.61 (d, 2H, AB type, J=17.5 Hz, C2-H), 3.58 (s, 3H, —N—CH3), 3.88 (m, 4H, —S—CH2—CO, CH—CH3), 4.15, 4.35 (d, 2H, AB type, J=12.5 Hz, —CH2—S—), 5.02 (d, 1H, J=5.0 Hz, C6-H), 5.54 (d, 1H, J=4.5 Hz, C7-H), and 9.38 (s, 1H, —NH—).

Example 7

100 ml of methylene dichloride, 100 ml of acetone and 2 g of the intermediate prepared according to Example 1 were added to a three-neck flask. 1.4 ml of diethylamine was dropwise added to the flask to dissolve the solid and to adjust the pH value within the range of 5.0-7.5. 0.8 g of N,N'-diisopropylthiourea was added to the flask and the mixture was refluxed until the completion of the reaction. Crystallization, filtration and drying under vacuum yielded 2.3 g of the product. Its $H^1$—NMR data is the same as those in Example 6.

III. Pharmacokinetic Comparative Experiments

The resulting BYS02 obtained from the Examples 6 and 7 as shown above was used to compare with cefathiamidine in the following pharmacokinetic study.

Commercially available cefathiamidine was used as the comparison in the pharmacokinetic study. Using the crossover controlled trial experimental design, 6 healthy Beagle dogs were divided into two groups: one group of dogs were intravenously injected with 50 mg/kg.bw of the BYS02 and the other group of dogs were injected with 50 mg/kg.bw of cefathiamidine. Blood samples were taken every 12 hours. The drug plasma concentrations were analyzed using HPLC. The drug plasma concentration over the time data were analyzed using MCPKP program.

Materials and Method

1. Animals

Six Beagle dogs were provided by Guangzhou Pharmaceutical Research Institute. They were healthy, male, one-year old, and each weighed 8.0±0.1 kg. The dogs were kept in single-dog cages and fed with water and food according to the standards for laboratory animals. One week before the tests, the dogs were examined for hearts, livers, and kidneys, and they were found normal.

2. Test Drugs, Agents, and Instruments

BYS02 was prepared according to Example 6 with a purity of 90%. Cefathiamidine was purchased from the market. Heparin sodium, sodium hydrogen phosphate, citric acid, methanol, ethyl acetate and other agents used were analytical-pure. Propionitrile used was chromatographic-pure. Water is pure. High Performance Liquid Chromatography (HPLC) and high-speed refrigerated centrifuges were used in the tests.

3. Drug Administration and Blood Sampling

Sixteen hours before and 4 hours after the administration, the Beagle dogs were not allowed to eat food but allowed to drink water freely. After intravenously injection with 50 mg/kg.bw of the BYS02 and cefathiamidine, respectively, the two groups of dogs were taken 3 ml of blood samples intravenously at 0, 0.083, 0.17, 0.25, 0.5, 1, 1.5, 2, 3, 4, 6, 9, and 12 hours. The dogs were administrated every other week and blood samples were collected according to the above schedule. The blood samples were added to centrifuge tubes, mixed with heparin, centrifuged at 4000 rpm for 10 minutes, and the serum samples were stored in a refrigerator at −20° C. until they were used.

4. HPLC Conditions

Hypersil ODS2, C18 column (4.6 mm×150 mm, 5 μm); mobile phase: propionitrile/phosphate buffer (11/89 volume ratio); wavelength: 254 nm; flow rate: 1.0 ml/min; room temperature; sample size: 20 μl.

Preparation of phosphate buffer (pH 7.0): 2.76 g of sodium hydrogen phosphate, 1.29 g of citric acid and 1000 ml of water were mixed well and filtered.

5. Statistic Analysis

Drug plasma concentration over the time data were analyzed using MCPKP program to calculate the pharmacokinetic parameters. The average values and standard deviations were also calculated.

6. Results

The drug plasma concentration over the time data after intravenous injection of the BYS02 satisfies the open three-compartment model. The main pharmacokinetic parameters are: Co=208.97±61.16 μg/mL, $t_{1/2\alpha}$=0.63±0.12 h, $t_{1/2\beta}$=2.19±0.04 h, AUC=108.29±18.17 mg/L·h, $V_1$=0.25±0.07 L/kg, $V_B$=1.61±0.30 L/kg, $Cl_B$=0.47±0.09 L/kg/h. The drug plasma concentration over the time data after intravenous injection of the cefathiamidine satisfies the open two-compartment model. The main pharmacokinetic parameters are: Co=90.84±29.71 μg/mL, $t_{1/2\alpha}$=0.21±0.14 h, $t_{1/2\beta}$0=0.65±0.03 h, AUC=42.25±1.02 mg/L·h, $V_1$=0.59±0.20 L/kg, $V_B$=1.11±0.07 L/kg, $Cl_B$=1.18±0.03 L/kg/h.

Figure 1:
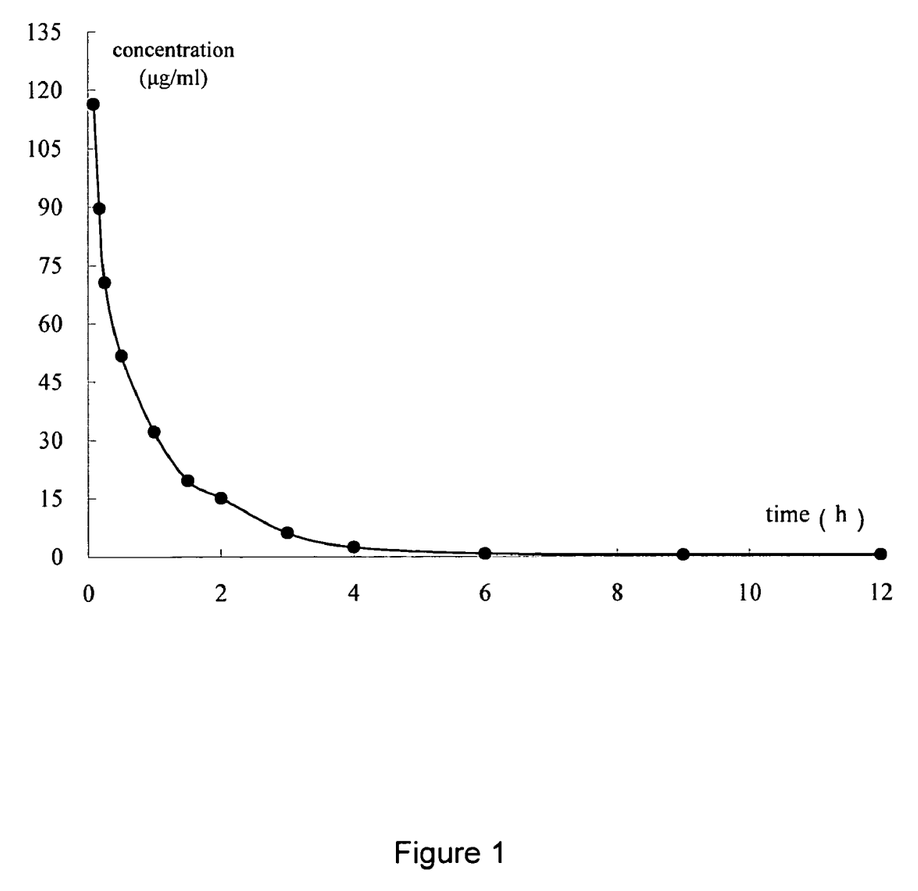
FIG. 1 illustrates the average plasma concentration of BYS02 over the time curve of Beagle dogs after administration of 50 mg/kg.bw (wherein "bw" means body weight) of BYS02.
Figure 2:
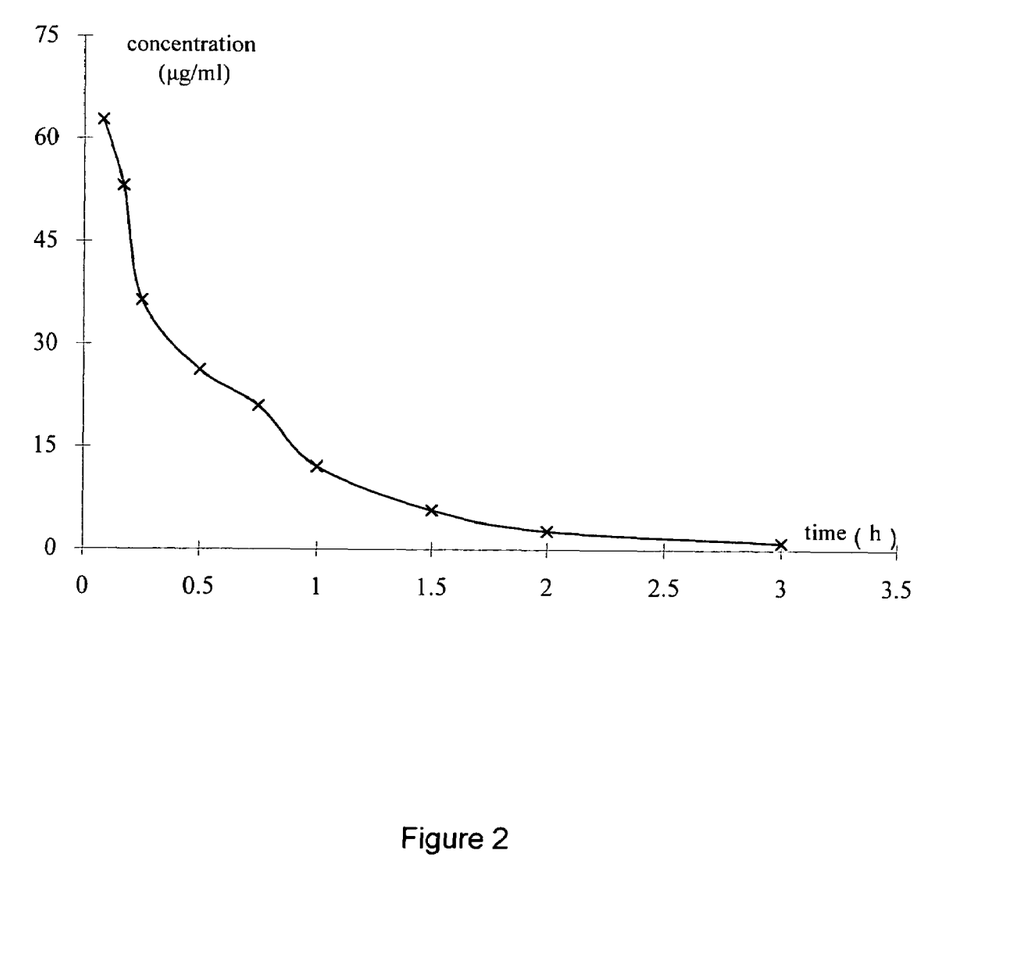
FIG. 2 illustrates the average plasma concentration of cefathiamidine over the time curve of Beagle dogs after administration of 50 mg/kg.bw of cefathiamidine.

For the same amount of intravenous injection, the half-life of the BYS02, i.e., 2.19±0.04 h, is significantly longer than that of cefathiamidine, i.e., 0.65±0.03 h. The clearance rate of the BYS02, i.e., 0.47±0.09 L/kg/h, is significantly lower than that of cefathiamidine, i.e., 1.18±0.03 L/kg/h. In addition, the AUC value of the BYS02 is significantly greater than that of cefathiamidine. In other words, the bioavailability of the BYS02 is greater than that of cefathiamidine. The average drug plasma concentration over the time curves of the BYS02 and cefathiamidine are shown in FIGS. 1 and 2, respectively.

IV. Acute Toxicity

A commonly-used acute toxicity test method was used with SPF grade mice by intravenous injection. The acute toxicity test of the BYS02 in mice indicated that the LD50 of a single intravenous administration is 672 mg/kg.bw with 95% confidence limit of 650-700 mg/kg.bw. The survived animals did not appear to be active. After a single intravenous injection of 930 mg/kg.bw or more, the animals died after 10 seconds of struggling. No death of the animals were found after single intravenous injection of 465 mg/kg.bw, which indicates that the toxicity of the BYS02 is not great.

The following examples illustrate the preparation of 3-[[[5-(carboxymethyl)-4-methyl-2-thiazolyl]thio]methyl]-7-[[[[[(1-methylethyl)amino][(1-methylethyl)imino]methyl]thio]acetyl]amino]-8-oxo-5-thia-1-aza-bicyclo[4.2.0]oct-2-en e-2-carboxylic acid, which has the following structure:

I. Preparation of Intermediate 5 g (0.0124 mol) of 7-amino-3-[[[5-(carboxymethyl)-4-methyl-2-thiazolyl]thio]methyl]-8-oxo-5-thia-1-aza-bicyclo [4.2.0]oct-2-ene-2-carboxylic acid ("7-TACS") was dissolved in 50 ml of acetone and 80 ml of water with stirring at a temperature of 0-5° C. 1.8 ml (0.013 mole) of triethylamine was added to the mixture dropwise to form a clear solution. After the solid is completely dissolved, 3.5 g of $NaHCO_3$ was gradually added to the solution and at the same time, 2.3 ml (0.026 mole) of bromoacetyl bromide was dropwise added to the solution. After the addition, the reaction continued for 1.5 hours. 1 g of active carbon was added to the reaction mixture with stirring for 0.5 hour to discolor the mixture. The active carbon was filtered out and washed with water. The aqueous solutions were collected and acidified with 3N of hydrochloric acid to a pH value of 2-2.5. Solid product was thus formed and crystallized at a temperature of 0-5° C. for 1 hour. The solid was filtered, washed with water until the pH value reaches 3, and dried under vacuum (less than 0.08 MPa) to yield 5 g of the intermediate (77% of yield).

II. Preparation of Product 5 g (0.0096 mole) of the intermediate as prepared above was dissolved in methylene dichloride with stirring at a temperature of 0-5° C. Triethylamine was dropwise added to the mixture, which became clear after 0.5 hours. 1.9 g (0.0118 mole) of N,N'-diisopropylthiourea was added to the clear solution and the temperature was raised to 38-40° C. until N,N'-diisopropylthiourea was completely dissolved. The solution was refluxed about 0.5 hours and a yellow solid product was formed. The reaction temperature was kept at the same reading for 1.5 hours, and then the reaction mixture was cooled to 0-5° C. to crystallize the product for 1 hour. The solid was filtered, washed twice with methylene dischloride (10 ml for each wash) and twice with acetone (75 ml for each wash), and dried under vacuum (less than 0.08 MPa) at 35° C. to yield 4.3 g of the product (75% yield).

The following compounds of formulae III and IV were prepared according to the preparation methods of the BYS02 as shown above using the commercially available intermediates VI.

Compound VI has the following general structure:

VI wherein: $R_1$ is selected from and

Compound III has the following general structure:

III

HNMR data are as follows: 3.03, 3.60 (d, 2H, AB type, J=17.5 Hz, C2-H), 5.00 (d, 1H, J=5.9 Hz, C6-H), 5.56 (d, 1H, J=4.5 Hz, C7-H), and 9.36 (s, 1H, —NH—).

Compound IV has the following general structure:

IV

HNMR data are as follows: 3.05, 3.63 (d, 2H, AB type, J=17.5 Hz, C2-H), 5.04 (d, 1H, J=5.9 Hz, C6-H), 5.56 (d, 1H, J=4.5 Hz, C7-H), and 9.40 (s, 1H, —NH—).

What is claimed is:

1. A cephalosporin compound comprising a C3 thio-methyl moiety substituted with an N-containing heterocyclic group, and a C7 thiourea acetamido group, or a pharmaceutically acceptable salt thereof, wherein said cephalosporin compound has the following formula I:

I wherein $R_1$ is selected from the following groups:

; and wherein $R_2$ is selected from the following groups:

2. The cephalosporin compound of claim 1, wherein the cephalosporin compound is chosen from the compounds of formulae II-V

II

III

IV and

V

3. A method of preparing the cephalosporin compound of claim 1, comprising:
(a) dissolving or suspending a starting cephalosporin compound comprising a C7 amino group and a C3 $CH_2$—$R_1$ group in a solvent and adjusting the pH value of the mixture with at least one base chosen from organic and inorganic bases to obtain a solution, wherein $R_1$ is defined as in claim 1;
(b) reacting the resulting solution with bromoacetyl bromide;
(c) acidifying the reaction mixture of step (b);
(d) reacting the resulting solution of step (c) with an N,N'-bissubstituted thiourea, wherein the N,N'-bissubstituted thiourea is selected from the following groups, -continued and (e) isolating the resulting product from the reaction mixture of step (d).

4. The method of claim 3, wherein the solvent in step (a) is selected from ketones, alcohols, alkyl halides, and mixtures thereof.

5. The method of claim 3, wherein the organic base in step (a) is selected from triethylamine, diethylamine, tributylamne, tetramethyl guanidine, and mixtures thereof.

6. The method of claim 3, wherein the inorganic base is selected from sodium carbonate, sodium bicarbonate, ammonium, and mixtures thereof.

7. The method of claim 3, wherein in step (c), the acidification uses at least one acid chosen from hydrochloric acid, sulfuric acid, acetic acid, and phosphoric acid.

8. A cephalosporin intermediate, wherein said intermediate has the general structure VII:

VII wherein $R_1$ is selected from the following groups:

and

9. A method for preparing the cephalosporin intermediate of claim 8, comprising reacting bromoacetyl bromide with compound VI

VI wherein $R_1$ is selected from the following groups:

-continued and

10. A pharmaceutical composition comprising (a) at least one compound chosen from the cephalosporin compounds of claim 1 and pharmaceutically acceptable salts thereof, and (b) a pharmaceutical acceptable carrier.

11. A pharmaceutical composition comprising (a) at least one compound chosen from the cephalosporin compounds of claim 1 and pharmaceutically acceptable salts thereof, and (b) a pharmaceutical acceptable carrier, wherein the pharmaceutical composition is an antibiotic.

12. The pharmaceutical composition of claim 10, wherein the pharmaceutical composition is in a form chosen from a pill, tablet, lozenge, coated tablet, granule, capsule, hard or soft gelatin capsule, aqueous solution, alcoholic solution, oily solution, syrup, emulsion suspension pastille suppository, solution for injection or infusion, ointment, tincture, cream, lotion, powder, spray, transdermal therapeutic systems, nasal spray, aerosol mixture, microcapsule, implant, rod or plaster.

13. A pharmaceutical composition comprising (a) at least one compound chosen from the cephalosporin compounds of claim 2 and pharmaceutically acceptable salts thereof, and (b) a pharmaceutical acceptable carrier.

14. A pharmaceutical composition comprising (a) at least one compound chosen from the cephalosporin compounds of claim 2 and pharmaceutically acceptable salts thereof, and (b) a pharmaceutical acceptable carrier, wherein the pharmaceutical composition is an antibiotic.

15. The pharmaceutical composition of claim 13, wherein the pharmaceutical composition is in a form chosen from a pill, tablet, lozenge, coated tablet, granule, capsule, hard or soft gelatin capsule, aqueous solution, alcoholic solution, oily solution, syrup, emulsion suspension pastille suppository, solution for injection or infusion, ointment, tincture, cream, lotion, powder, spray, transdermal therapeutic systems, nasal spray, aerosol mixture, microcapsule, implant, rod and plaster.

16. A method of treating a bacterial infection comprising administering to a patient in need thereof the pharmaceutical composition of claim 10.

17. A method of treating a bacterial infection comprising administering to a patient in need thereof the pharmaceutical composition of claim 13.

18. The method of claim 16, wherein the bacterial infection is an antibiotic-resistant disease.

19. The method of claim 17, wherein the bacterial infection is an antibiotic-resistant disease.

* * * * *

UNITED STATES PATENT AND TRADEMARK OFFICE
CERTIFICATE OF CORRECTION

PATENT NO. : 7,700,581 B2
APPLICATION NO. : 11/700087
DATED : April 20, 2010
INVENTOR(S) : Mao Chen et al.

It is certified that error appears in the above-identified patent and that said Letters Patent is hereby corrected as shown below:

Title Page, Item (73), lines 1-3, "Assignee: Guangzhou Baiyunshan Pharmaceutical Co., Ltd., Guangzhou, Guangdong (CN)" should read --Assignee: Guangzhou Baiyunshan Pharmaceutical Co., Ltd., Guangzhou, Guangdong (CN) and Guangzhou Baiyunshan Pharmaceutical Co., Ltd. Guangzhou Baiyunshan Pharmaceutical Factory, Guangzhou, Guangdong (CN)--.

Signed and Sealed this

Thirty-first Day of August, 2010

David J. Kappos
*Director of the United States Patent and Trademark Office*